(12) United States Patent
Ikemoto et al.

(10) Patent No.: US 9,468,356 B2
(45) Date of Patent: Oct. 18, 2016

(54) LESION EVALUATION INFORMATION GENERATOR, AND METHOD AND COMPUTER READABLE MEDIUM THEREFOR

(71) Applicants: HOYA CORPORATION, Tokyo (JP); Kyoto University, Kyoto (JP)

(72) Inventors: Yousuke Ikemoto, Tokyo (JP); Hiroshi Nakase, Kyoto (JP); Minoru Matsuura, Kyoto (JP); Takuya Yoshino, Kyoto (JP); Hirokazu Higuchi, Kyoto (JP)

(73) Assignees: HOYA CORPORATION, Tokyo (JP); KYOTO UNIVERSITY, Kyoto (JP)

( * ) Notice: Subject to any disclaimer, the term of this patent is extended or adjusted under 35 U.S.C. 154(b) by 310 days.

(21) Appl. No.: 14/260,599

(22) Filed: Apr. 24, 2014

(65) Prior Publication Data

US 2014/0320620 A1   Oct. 30, 2014

(30) Foreign Application Priority Data

Apr. 26, 2013   (JP) .................................. 2013-094730

(51) Int. Cl.
*A61B 1/04* (2006.01)
*A61B 1/00* (2006.01)
(Continued)

(52) U.S. Cl.
CPC ......... *A61B 1/00009* (2013.01); *A61B 1/0005* (2013.01); *G06T 7/0014* (2013.01); *G06T 7/408* (2013.01); *G06T 2207/10024* (2013.01); *G06T 2207/10068* (2013.01); *G06T 2207/30096* (2013.01)

(58) Field of Classification Search
CPC ...................................................... A61B 1/04
See application file for complete search history.

(56) References Cited

U.S. PATENT DOCUMENTS 5,592,216 A   1/1997   Uehara et al.
8,274,558 B2  9/2012   Takayama
(Continued)

FOREIGN PATENT DOCUMENTS

CN   101964873   2/2011
CN   102117484   7/2011
(Continued)

OTHER PUBLICATIONS

Office Action issued in China Counterpart Patent Appl. No. 201410168802.3, dated Aug. 2, 2016, along with an english translation thereof.

*Primary Examiner* — Dave Czekaj
*Assistant Examiner* — Nam Pham
(74) *Attorney, Agent, or Firm* — Greenblum & Bernstein, P.L.C.

(57) ABSTRACT

A lesion evaluation information generator including a processor configured to, when executing processor-executable instructions stored in a memory, determine a hue value and a saturation value of each of pixels of an endoscopic image based on an acquired endoscopic color image data, determine, for at least a part of the pixels of the endoscopic image, a correlation value between color information of each individual pixel and reference color data, based on a hue correlation value between the hue value of each individual pixel and a reference hue value of the reference color data, and a saturation correlation value between the saturation value of each individual pixel and a reference saturation value of the reference color data, and generate an evaluation value for evaluating a severity of a lesion in the endoscopic image, by integrating the correlation value of each individual pixel.

14 Claims, 9 Drawing Sheets

(51) Int. Cl.
*G06T 7/00* (2006.01)
*G06T 7/40* (2006.01)

(56) References Cited

U.S. PATENT DOCUMENTS

| | | |
|---|---|---|
| 8,665,347 B2 | 3/2014 | Miyawaki et al. |
| 8,790,251 B2 | 7/2014 | Yamaguchi |
| 8,805,061 B2 | 8/2014 | Tsuruoka |
| 2005/0078175 A1 | 4/2005 | Kaneko |
| 2006/0252988 A1 | 11/2006 | Ayame et al. |
| 2007/0191677 A1 | 8/2007 | Nishimura et al. |
| 2011/0032389 A1 | 2/2011 | Miyawaki et al. |
| 2011/0069868 A1 | 3/2011 | Tsuruoka |
| 2011/0222755 A1 | 9/2011 | Kimura |
| 2011/0237915 A1 | 9/2011 | Yamaguchi |
| 2013/0030268 A1 | 1/2013 | Saito |
| 2013/0094726 A1* | 4/2013 | Kitamura ............ G06T 7/0012 382/128 |

FOREIGN PATENT DOCUMENTS

| | | |
|---|---|---|
| CN | 102197984 | 9/2011 |
| CN | 102894948 | 1/2013 |
| EP | 1857042 | 11/2007 |
| JP | 2003-334162 | 11/2003 |
| JP | 2006-122502 | 5/2006 |
| JP | 2009-106424 | 5/2009 |
| JP | 2014-18332 | 2/2014 |
| JP | 2014-18333 | 2/2014 |
| WO | 02/073507 | 9/2002 |
| WO | 2009/145157 | 12/2009 |

* cited by examiner

LESION EVALUATION INFORMATION GENERATOR, AND METHOD AND COMPUTER READABLE MEDIUM THEREFOR

BACKGROUND OF THE INVENTION

The present invention relates to techniques for an apparatus configured to evaluate a severity of a lesion of a patient, particularly, for a lesion evaluation information generator configured to generate evaluation information for evaluating the severity of the lesion based on color information of an endoscopic color image.

In general, a lesion has a color different from a color of normal mucous tissue. With improvement in performance of a color endoscope apparatus, it is becoming possible to identify a lesion having a color slightly different from a color of normal tissue. However, in order to acquire an ability to distinguish the lesion from the normal tissue based on such a slight color difference in an endoscopic image, an operator of the color endoscope apparatus needs to be trained by a skilled person over a long period of time. Further, it is not easy even for a skilled operator to distinguish the lesion from the normal tissue based on such a slight color difference, and it requires careful operations. In view of the problems, an electronic endoscope apparatus has been proposed that is configured to perform a color conversion process of highlighting color differences in endoscopic image data captured with white light, so as to make it easier to identify a lesion (e.g., see Japanese Patent Provisional Publication No. 2009-106424, which may hereinafter be referred to as the '424 Publication).

SUMMARY OF THE INVENTION

An image generated by the electronic endoscope apparatus disclosed in the '424 Publication makes it easier to distinguish a lesion from normal tissue than a usual endoscopic image. Nonetheless, the lesion shows a subtle color change depending on a severity of the lesion. Therefore, even though an inexperienced operator is allowed to distinguish the lesion from the normal tissue using known technologies such as the technique disclosed in the '424 Publication, it is difficult for the inexperienced operator to exactly evaluate the severity of the lesion. Furthermore, it is impossible even for a skilled operator to make an objective and reproducible evaluation (independent of a skill level of the operator). This is because it generally depends on image reading skills based on experiences and knowledge of individual operators whether the severity of the lesion is properly evaluated.

Aspects of the present invention are advantageous to present one or more improved techniques, for a lesion evaluation information generator, which make it possible to conduct an objective and reproducible evaluation of a severity of a lesion.

According to aspects of the present invention, a lesion evaluation information generator is provided, which includes an image data acquirer configured to acquire endoscopic color image data that represents an endoscopic image showing a lesion, a memory, and a processor configured to, when executing processor-executable instructions stored in the memory, provide a color information determiner configured to determine a hue value and a saturation value of each of pixels included in the endoscopic image based on the acquired endoscopic color image data, a correlation value determiner configured to determine, for at least a part of the pixels of the endoscopic image, a correlation value that represents a correlation between color information of each individual pixel and reference color data, based on a hue correlation value that represents a correlation between the determined hue value of each individual pixel and a reference hue value of the reference color data, and a saturation correlation value that represents a correlation between the determined saturation value of each individual pixel and a reference saturation value of the reference color data, and an evaluation value generator configured to generate an evaluation value for evaluating a severity of the lesion in the endoscopic image, by deriving a summation of the correlation values from integrating the correlation value determined for each individual pixel.

According to aspects of the present invention, further provided is a method configured to be implemented by a processor coupled with an image data acquirer configured to acquire endoscopic color image data that represents an endoscopic image showing a lesion, the method including determining a hue value and a saturation value of each of pixels included in the endoscopic image based on the acquired endoscopic color image data, determining, for at least a part of the pixels of the endoscopic image, a correlation value that represents a correlation between color information of each individual pixel and reference color data, based on a hue correlation value that represents a correlation between the determined hue value of each individual pixel and a reference hue value of the reference color data, and a saturation correlation value that represents a correlation between the determined saturation value of each individual pixel and a reference saturation value of the reference color data, and generating an evaluation value for evaluating a severity of the lesion in the endoscopic image, by deriving a summation of the correlation values from integrating the correlation value determined for each individual pixel.

According to aspects of the present invention, further provided is a non-transitory computer readable medium storing processor-executable instructions configured to, when executed by a processor coupled with an image data acquirer configured to acquire endoscopic color image data that represents an endoscopic image showing a lesion, cause the processor to determine a hue value and a saturation value of each of pixels included in the endoscopic image based on the acquired endoscopic color image data, determine, for at least a part of the pixels of the endoscopic image, a correlation value that represents a correlation between color information of each individual pixel and reference color data, based on a hue correlation value that represents a correlation between the determined hue value of each individual pixel and a reference hue value of the reference color data, and a saturation correlation value that represents a correlation between the determined saturation value of each individual pixel and a reference saturation value of the reference color data, and generate an evaluation value for evaluating a severity of the lesion in the endoscopic image, by deriving a summation of the correlation values from integrating the correlation value determined for each individual pixel.

BRIEF DESCRIPTION OF THE ACCOMPANYING DRAWINGS

Figure 10:
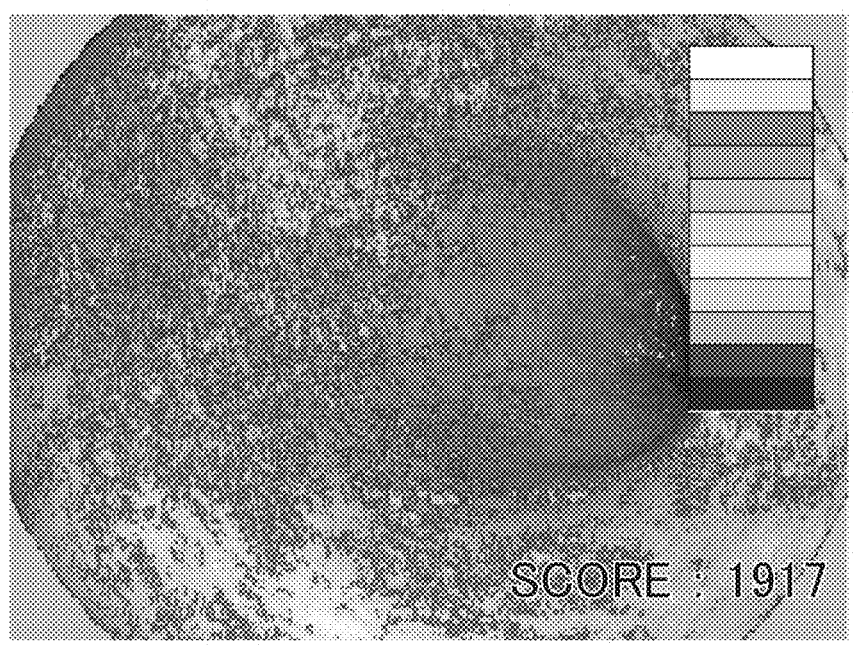

FIG. 10 exemplifies an evaluation image displayed on a screen of a monitor in the embodiment according to aspects of the present invention.

DETAILED DESCRIPTION OF THE EMBODIMENTS

It is noted that various connections are set forth between elements in the following description. It is noted that these connections in general and, unless specified otherwise, may be direct or indirect and that this specification is not intended to be limiting in this respect. Aspects of the invention may be implemented on circuits (such as application specific integrated circuits) or in computer software as programs storable on computer readable media including but not limited to RAMs, ROMs, flash memories, EEPROMs, CD-media, DVD-media, temporary storage, hard disk drives, floppy drives, permanent storage, and the like.

Hereinafter, an embodiment according to aspects of the present invention will be described with reference to the accompanying drawings.

Figure 1:
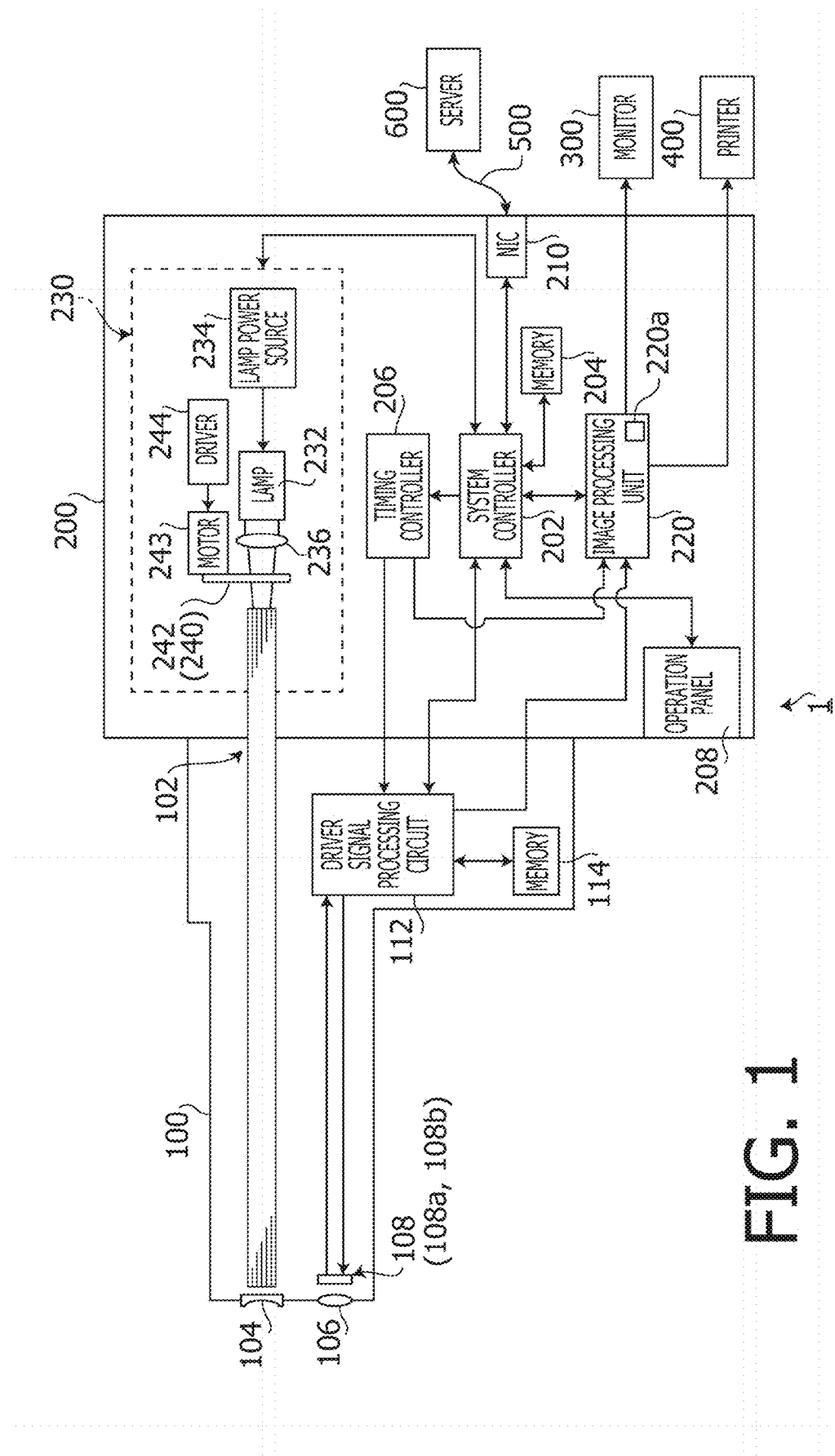
FIG. 1 is a block diagram showing a configuration of an electronic endoscope apparatus in an embodiment according to aspects of the present invention.

FIG. 1 is a block diagram showing a configuration of an electronic endoscope apparatus 1 in the embodiment. As shown in FIG. 1, the electronic endoscope apparatus 1 includes an electronic scope 100, a processor 200, a monitor 300, and a printer 400.

The processor 200 includes a system controller 202 and a timing controller 206. The system controller 202 is configured to execute processor-executable programs stored in a memory 204, and take overall control of the electronic endoscope apparatus 1. Further, the system controller 202 is configured to update various settings for the electronic endoscope apparatus 1 in response to an instruction input by a user (such as an operator or an assistant) through an operation panel 208. The timing controller 206 is configured to transmit, to circuits in the electronic endoscope apparatus 1, clock pulses for adjusting timings of processing/operations by individual elements included in the electronic endoscope apparatus 1.

The processor 200 includes a light source 230 configured to supply illumination light to the electronic scope 100. The light source 230 includes a lamp 232, a lamp power source 234, a converging lens 236, and a light amount adjuster 240. The lamp 232 is a high luminance lamp configured to emit white illumination light when supplied with a driving electric power from the lamp power source 234. For instance, examples of the lamp 232 may include (but are not limited to) a Xenon lamp, a metal halide lamp, a mercury lamp, and a halogen lamp. The illumination light emitted by the lamp 232 is converged by the converging lens 236, and then rendered incident onto an incident end face of an LCB (Light Carrying Bundle) 102 of the electronic scope 100 via the light amount adjuster 240.

The light amount adjuster 240 is configured to adjust an amount of the illumination light incident onto the incident end face of the LCB 102 under the control of the system controller 202. The light amount adjuster 240 includes a diaphragm 242, a motor 243, and a driver 244. The driver 244 is configured to generate a driving current for driving the motor 243, and supply the driving current to the motor 243. The diaphragm 242 is configured to, when driven by the motor 243, change a variable opening and adjust the amount of the illumination light transmitted through the opening.

The illumination light, introduced into the LCB 102 via the incident end face, is transmitted through the LCB 102 and emitted from an exit end face of the LCB 102 that is disposed in a distal end portion of the electronic scope 100. Then, the illumination light is rendered incident onto a subject via a light distribution lens 104. Reflected light from the subject is transmitted through an objective lens 106 to form an optical image on a light receiving surface of a solid-state image sensor 108.

The solid-state image sensor 108 is a single color CCD (Charge-Coupled Device) image sensor that includes various filters, such as an IR (Infrared) cut-off filter 108a and a Bayer array color filter 108b, arranged on the light receiving surface of the sensor 108. The solid-state image sensor 108 is configured to generate primary color signals of R (Red), G (Green), and B (Blue) corresponding to the optical image formed on the light receiving surface.

The electronic scope 100 further includes a driver signal processing circuit 112 disposed inside a joint portion of the electronic scope 100. The driver signal processing circuit 112 is configured to perform predetermined signal processing (such as color interpolation, a matrix operation, and Y/C separation) for the primary color signals received from the solid-state image sensor 108, to generate image signals (such as a luminance signal Y, and color difference signals Cb and Cr), and to transmit the generated image signals to an image processing unit 220 of the processor 200. The driver signal processing circuit 112 is configured to access a memory 114 to read out specific information of the electronic scope 100. The specific information of the electronic scope 100 includes, for example, the number of pixels, sensitivity, an available frame rate, and a model number of the solid-state image sensor 108. The driver signal processing circuit 112 is further configured to transmit, to the system controller 202, the specific information read out from the memory 114.

The system controller 202 is configured to perform various arithmetic operations based on the specific information of the electronic scope 100, and generate control signals. Further, the system controller 202 is configured to, using the generated control signals, control operations and timings of circuits in the processor 200 so as to execute processes suitable for the electronic scope 100 currently connected with the processor 200.

The timing controller 206 is configured to, according to the timing control by the system controller 202, supply clock pulses to the driver signal processing circuit 112 and the image processing unit 220. The driver signal processing circuit 112 is configured to, according to the clock pulses supplied from the timing controller 206, drive and control the solid-state image sensor 108 with timing synchronized with a frame rate for images to be processed by the processor 200.

The image processing unit 220 is configured to, under the control of the system controller 202, generate video signals to display images (such as endoscopic images) on a screen of the monitor 300 based on image signals received from the driver signal processing circuit 112, and transmit the generated video signals to the monitor 300. Thereby, the operator is allowed to make a diagnosis of tissue (e.g., inside a gastrointestinal tract) through an endoscopic image displayed on the screen of the monitor 300.

The processor 200 is connected with a server 600 via an NIC (Network Interface Card) 210 and a network 500. The processor 200 is configured to download, from the server 600, information on endoscopy (such as information on a patient's electronic medical record and information on the operator). The downloaded information may be displayed, e.g., on the screen of the monitor 300 or the operation panel 208. Further, the processor 200 is configured to upload, to the server 600, endoscopy results (such as endoscopic image data, endoscopy conditions, image analysis results, and clinical findings and viewpoints of the operator) to save the endoscopy results.

[Lesion Evaluation Information Generating Process]

Figure 2:
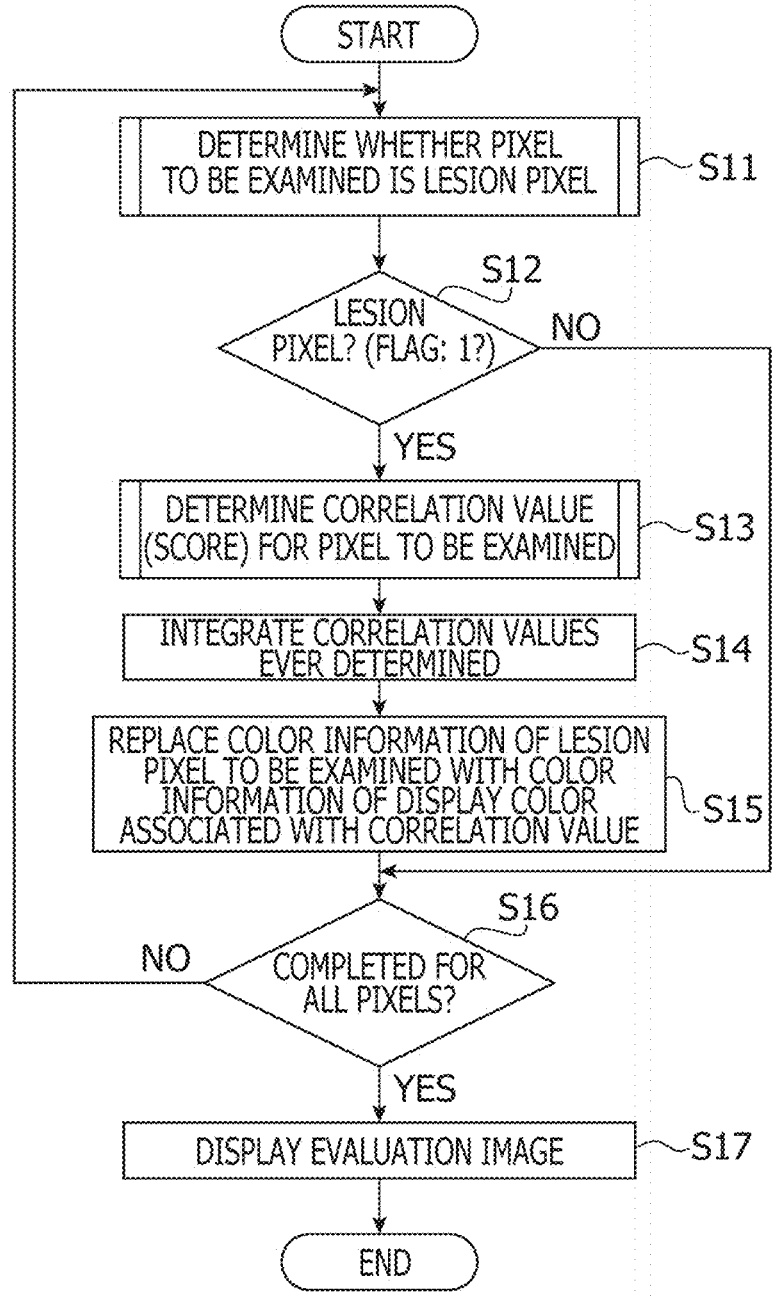
FIG. 2 is a flowchart showing a procedure of a lesion evaluation information generating process to be executed by a processor of the electronic endoscope apparatus in the embodiment according to aspects of the present invention.

FIG. 2 is a flowchart showing a procedure of a lesion evaluation information generating process to be executed by the processor 200. The below-described lesion evaluation information generating process is a process to perform an objective evaluation of a severity of a lesion (such as erythrochromia lesions including an edema and a hemorrhagic lesion) of an inflammatory bowel disease (IBD) within a field of view for imaging with the electronic scope 100. In the lesion evaluation information generating process, in general, it is determined for each individual pixel contained in endoscopic color image data whether a pixel to be examined is a pixel imaging a partial lesion (hereinafter referred to as a lesion pixel), e.g., in order of predetermined pixel addresses from a pixel located in an upper left corner of the light receiving surface. Then, a score is determined that represents a severity of the partial lesion imaged by the pixel determined as a lesion pixel. After the score has been determined for every lesion pixel, an evaluation value (evaluation information) for evaluating the severity of the lesion is determined based on all the determined scores. The evaluation value is reproducible numerical data to be determined by executing the lesion evaluation information generating process shown in FIG. 2. Therefore, by acquiring the evaluation value, the operator is allowed to make an objective evaluation of the severity of the lesion.

[S11 in FIG. 2 (Detection of Lesion Pixels)]

Figure 3:
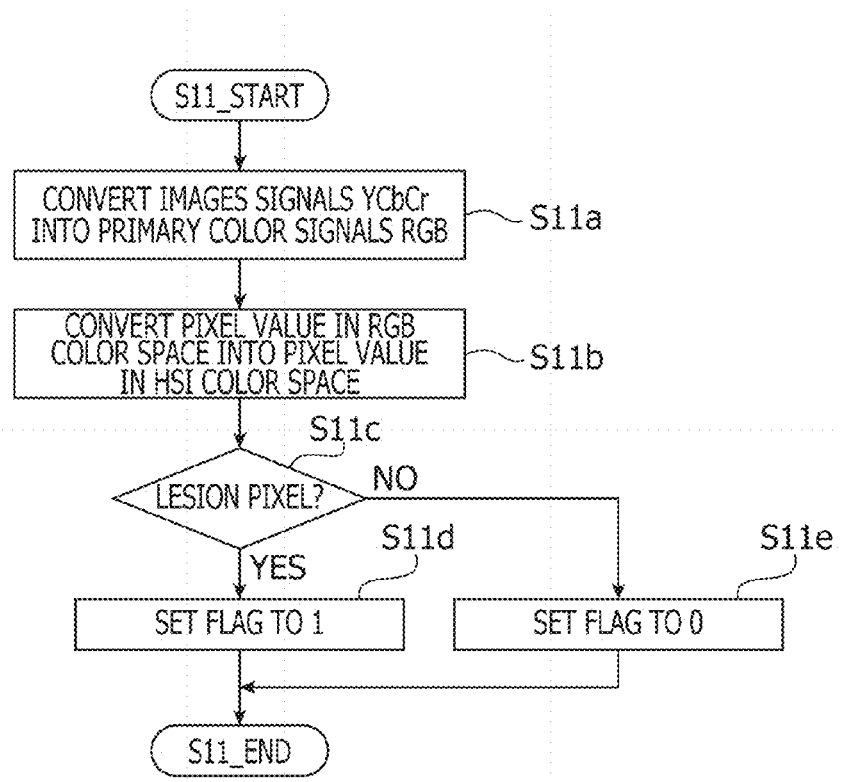
FIG. 3 is a flowchart showing a procedure of S11 (detection of lesion pixels) shown in FIG. 2 as a subroutine of the lesion evaluation information generating process in the embodiment according to aspects of the present invention.

In S11 of the lesion evaluation information generating process (see FIG. 2), the processor 200 determines whether a pixel (x, y) to be examined is a lesion pixel. By executing S11 to detect lesion pixels, pixels to be examined in the following steps are limited to the detected lesion pixels. Thereby, it is possible to reduce a total amount of operations to be executed in the lesion evaluation information generating process. FIG. 3 is a flowchart showing a procedure of S11 as a subroutine of the lesion evaluation information generating process.

(S11a in FIG. 3)

In S11a (see FIG. 3), for the pixel (x, y) to be examined, the processor 200 converts image signals (a luminance signal Y, and a color difference signals Cb and Cr) received from the driver signal processing circuit 112 into primary color signals (R, G, and B) with a predetermined matrix coefficient.

(S11b in FIG. 3)

In S11b, the processor 200 converts a pixel value (R (x, y), G (x, y), B (x, y)) in an RGB color space defined by the three primary colors R, G, and B into a pixel value (H (x, y), S (x, y), I (x, y)) in an HSI (Hue-Saturation-Intensity) color space defined by three factors Hue, Saturation, and Intensity. The converted pixel value (H (x, y), S (x, y), I (x, y)) is stored into a memory 220a in the image processing unit 220. It is noted that the pixel value (R (x, y), G (x, y), B (x, y)) in the RGB color space may be converted into a pixel value (H (x, y), S (x, y), V (x, y)) in an HSV (Hue-Saturation-Value) color space defined by three factors Hue, Saturation, and Value, instead of the pixel value (H (x, y), S (x, y), I (x, y)) in the HSI color space.

(S11c in FIG. 3)

Figure 4:
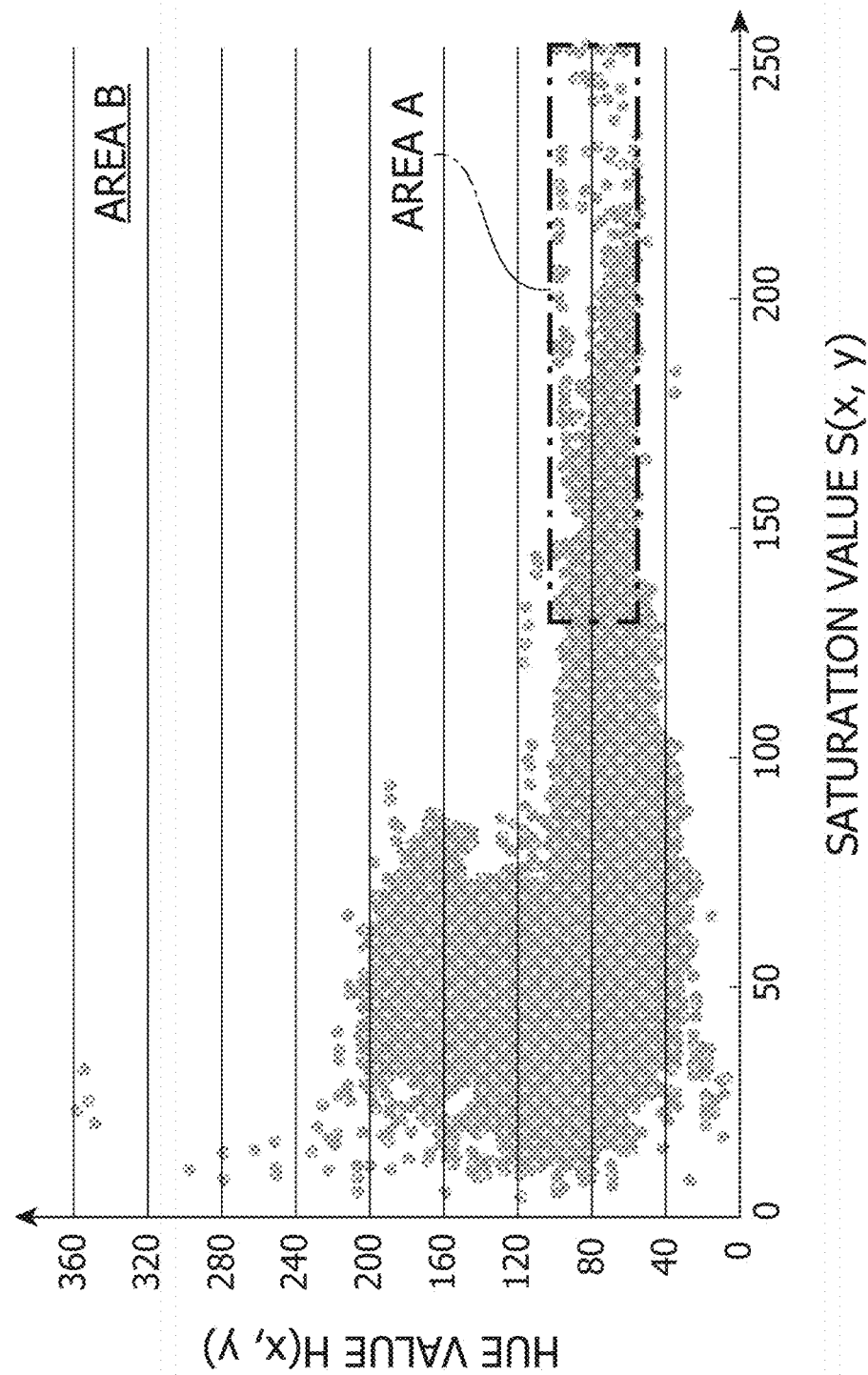
FIG. 4 is a scatter diagram obtained by plotting pixel data of biotissue images extracted from endoscopic image data of a plurality of patients of an inflammatory bowel disease (IBD) in the embodiment according to aspects of the present invention.

In S11c, the processor 200 determines whether the pixel (x, y) to be examined is a lesion pixel, based on H (x, y) (i.e., the hue of the pixel (x, y)) and S (x, y) (i.e., the saturation of the pixel (x, y)). FIG. 4 shows, as reference data used in S11c, a scatter diagram obtained by plotting pixel data (i.e., data pairs of H (x, y) and S (x, y)) of biotissue images extracted from endoscopic image data of a plurality of IBD patients. The scatter diagram shown in FIG. 4 is sectioned into an area A surrounded by a long dashed short dashed line and an area B other than the area A. The area A includes most of pixel data of pixels determined as pixels imaging inflamed sites of IBD by a doctor skilled at diagnostic endoscopy. The area B includes most of pixel data of pixels determined as pixels imaging normal sites by the doctor skilled at diagnostic endoscopy. Thus, the areas A and B are defined based on experiences and knowledge of the inventors, and thus regarded as research achievements (deliverables) of the inventors.

In S11c, the processor 200 determines whether the pixel data (H (x, y), S (x, y)) of the pixel (x, y) to be examined is to be plotted in the area A. Specifically, the processor 200 determines that the pixel data (H (x, y), S (x, y)) of the pixel (x, y) to be examined is to be plotted in the area A, when determining that the following expressions (1) and (2) are satisfied (S11c: Yes). Meanwhile, the processor 200 determines that the pixel data (H (x, y), S (x, y)) of the pixel (x, y) to be examined is not to be plotted in the area A, when determining that at least one of the expressions (1) and (2) is not satisfied (S11c: No). It is noted that, in the expressions (1) and (2), $\delta_{H1}$, $\delta_{S1}$, and $S_{S2}$ are correction values settable by the operator. The operator is allowed to adjust a rigor (a sensitivity) of the determination in S11c by changing the correction values $\delta_{H1}$, $\delta_{S1}$, and $\delta_{S2}$ as needed.

$$130 + \delta_{H1} \leq H(x, y) \quad \text{Expression (1)}$$

$$60 + \delta_{S1} \leq S(x, y) \leq 100 + \delta_{S2} \quad \text{Expression (2)}$$

(S11d in FIG. 3)

A pixel (x, y) having pixel data (H (x, y), S (x, y)) to be plotted in the area A is determined to be a pixel imaging an inflamed site of IBD (i.e., a lesion pixel) (S11c: Yes). The memory 220a stores a flag table, which contains a flag f (x, y) corresponding to each pixel (x, y) included in the endoscopic color image data. In S11d, the processor 200 sets to "1" a value of a flag f (x, y) corresponding to the pixel (x, y) determined to be a lesion pixel.

(S11e in FIG. 3)

Meanwhile, a pixel (x, y) having pixel data (H (x, y), S (x, y)) to be plotted in the area B is determined to be a pixel imaging normal tissue (S11c: No). In S11e, the processor 200 sets to "0" a value of a flag f (x, y) corresponding to the pixel (x, y) determined to be a pixel imaging normal tissue.

[S12 in FIG. 2 (Determination of Flag Value)]

In S12 (see FIG. 2), the processor 200 determines whether a value of the flag f (x, y) set in S11d or S11e is equal to "1." When determining that the value of the flag f (x, y) as set is equal to "1" (S12: Yes), the processor 200 goes to S13, in which the processor 200 determines (calculates) a score of the inflamed site for the pixel (x, y) to be examined. Meanwhile, when determining that the value of the flag f (x, y) as set is equal to "0" (S12: No), the processor 200 goes to S16 without executing S13 to S15, since the processor 200 does not need to determine a score for the pixel (x, y) to be examined.

[S13 in FIG. 2 (Determination of a Score for Each Lesion Pixel)]

Figure 5:
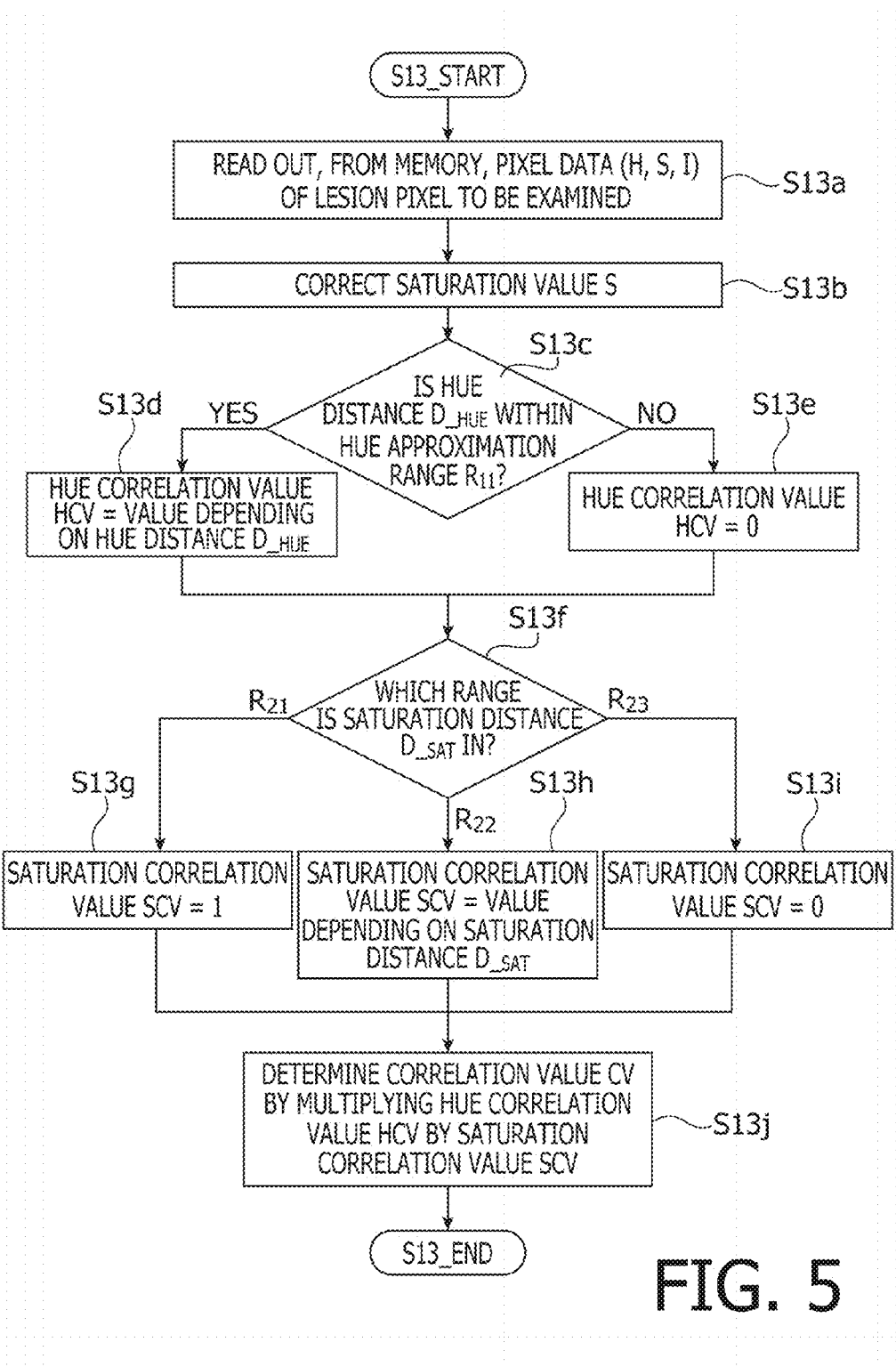
FIG. 5 is a flowchart showing a procedure of S13 (determination of a score for each lesion pixel) shown in FIG. 2 as a subroutine of the lesion evaluation information generating process in the embodiment according to aspects of the present invention.

In S13, the processor 200 determines (calculates) the score of the inflamed site for the pixel (x, y) to be examined. FIG. 5 is a flowchart showing a procedure of S13 as a subroutine of the lesion evaluation information generating process.

(S13a in FIG. 5)

In S13a (see FIG. 5), the processor 200 reads out, from the memory 220a, pixel data (H (x, y), S (x, y), I (x, y)) for the lesion pixel (x, y) to be examined.

(S13b in FIG. 5)

An illuminance of the illumination light for illuminating the subject is uneven to no small degree within the field of view. Further, it has been known that the inflammation of IBD is accompanied by dilation of blood vessels and leakage of a blood plasma component from the blood vessels, and normal mucous membranes in surfaces in an inflamed site drop off more with further symptom progression of IBD. Hence, it has also been known that the color of the inflamed site becomes closer to a blood color with further symptom progression of IBD. Further, it has been known that the saturation and the intensity of the blood color have a negative correlation with each other. From these facts, the inventors have acquired the following findings and knowledge. The intensity of the inflamed site contains potential errors due to the unevenness of the illuminance of the illumination light, and the errors in the intensity have influences on the saturation of the inflamed site of which the color is close to the blood color (namely, the saturation of the inflamed site has errors due to the unevenness of the illuminance of the illumination light). Thus, in S13b, the processor 200 corrects the saturation value S (x, y) of the lesion pixel (x, y) to be examined, based on the intensity value I (x, y). Specifically, in S13b, the saturation value S (x, y) is corrected based on the following expression (3).

$$\begin{bmatrix} INT_{-correction} \\ SAT_{-correction} \end{bmatrix} = \begin{bmatrix} \cos\theta & -\sin\theta \\ \sin\theta & \cos\theta \end{bmatrix} \begin{bmatrix} INT \\ SAT \end{bmatrix} + \begin{bmatrix} REFER_{-INT} \\ REFER_{-SAT} \end{bmatrix} \quad \text{Expression (3)}$$

In the expression (3), INT and SAT represent the intensity value I (x, y) and the saturation value S (x, y) of the lesion pixel (x, y) to be examined, respectively. $REFER_{INT}$ and $REFER_{SAT}$ represent an intensity value and a saturation value of blood sample data as reference values, respectively. $\theta$ represents an angle corresponding to a correlation coefficient between the intensity value and the saturation value of the blood sample data. $INT\_{correction}$ and $SAT\_{correction}$ represent a corrected intensity value and a corrected saturation value of the lesion pixel (x, y) to be examined, respectively. It is noted that the inventors found that the correlation coefficient between the intensity value and the saturation value of the blood sample data is determined to be −0.86 ($\theta$=149.32).

Thus, it is possible to correct the errors in the saturation value S (x, y) due to the unevenness of the luminance of the illumination light by correcting the saturation value S (x, y) using the intensity value I (x, y).

Figure 6A:
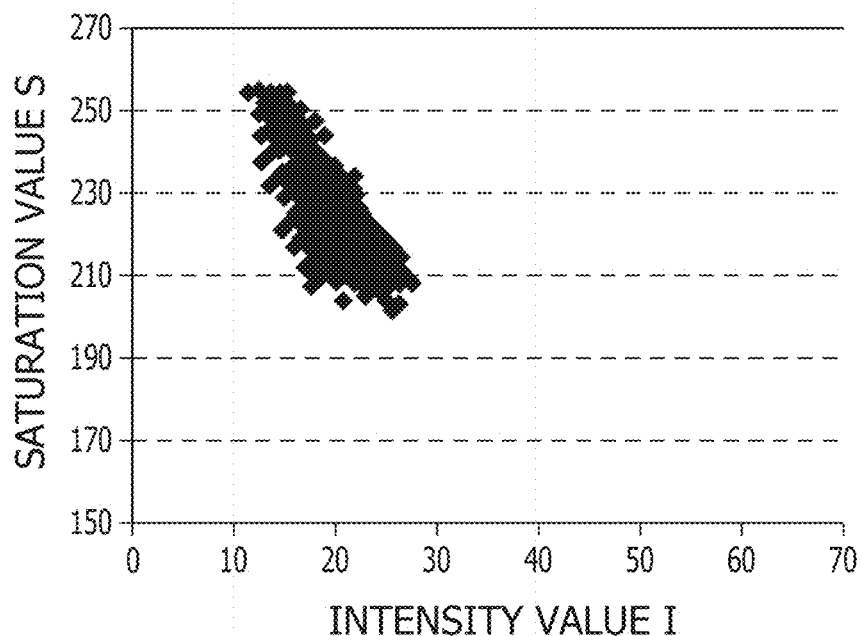
FIG. 6A is a scatter diagram, in which saturation values have not been corrected, of blood sample data taken from a plurality of IBD cases in the embodiment according to aspects of the present invention.
Figure 6B:
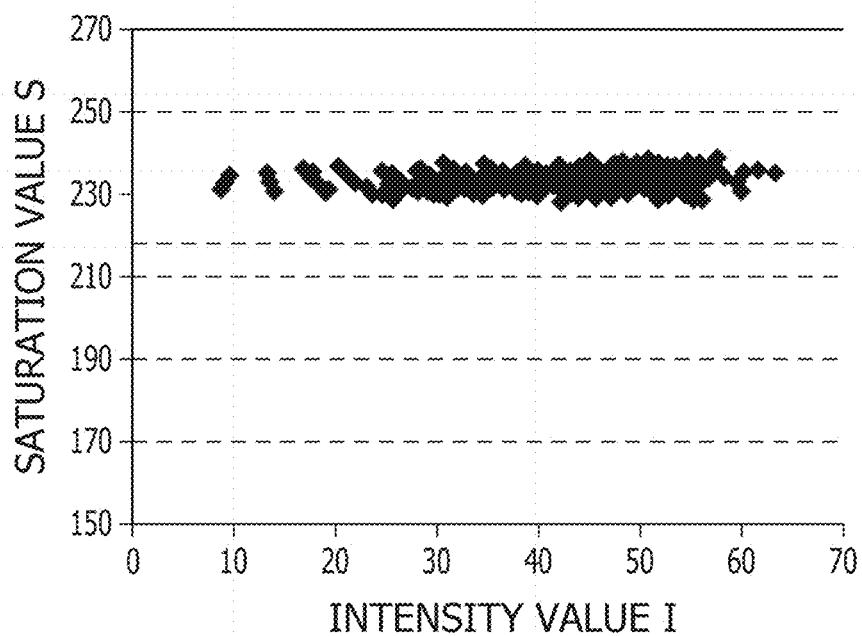
FIG. 6B is a scatter diagram, in which saturation values have been corrected, of the blood sample data taken from the plurality of IBD cases in the embodiment according to aspects of the present invention.

FIGS. 6A and 6B are scatter diagrams of blood sample data taken from a plurality of IBD cases. In FIGS. 6A and 6B, a vertical axis represents the saturation values S, and a horizontal axis represents the intensity value I. FIG. 6A is a scatter diagram in which saturation values S have not been corrected using the expression (3). FIG. 6B is a scatter diagram in which saturation values S have been corrected using the expression (3). As shown in FIG. 6A, the blood sample data have widely-varying saturation values S. Meanwhile, as shown in FIG. 6B, the correction using the expression (3) suppresses the variation in the saturation values S of the blood sample data. Namely, the saturation values S of the blood sample data are substantially constant regardless of the intensity values I thereof.

Figures 7A, 7B:
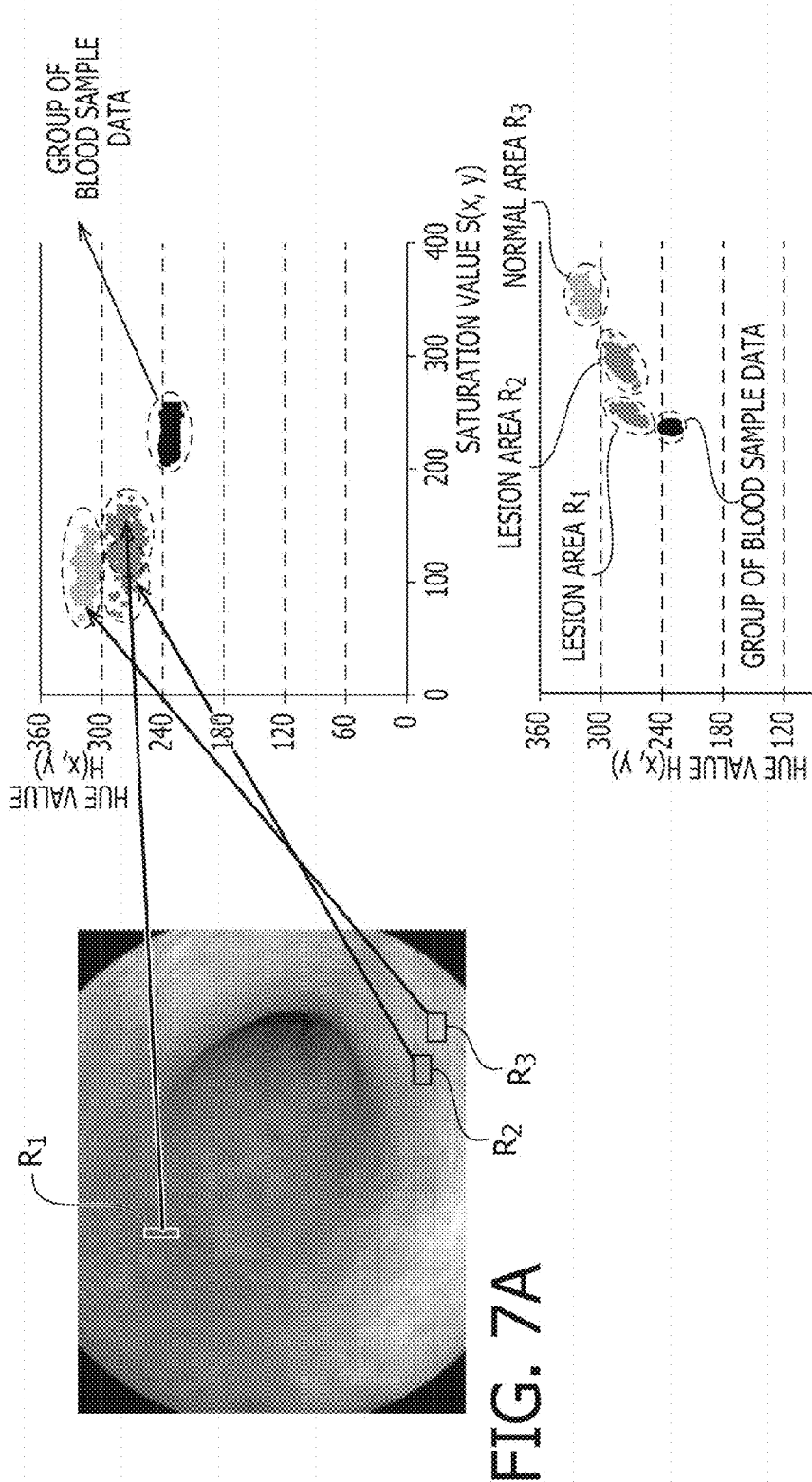
FIG. 7A is a scatter diagram (a distribution diagram), in which saturation values have not been corrected, of the blood sample data, and pixel data of lesion areas and normal areas in an endoscopic image in the embodiment according to aspects of the present invention.
FIG. 7B is a scatter diagram (a distribution diagram), in which saturation values have been corrected, of the blood sample data, and the pixel data of the lesion areas and the normal areas within the endoscopic image in the embodiment according to aspects of the present invention.

FIGS. 7A and 7B are scatter diagrams (distribution diagrams) for the blood sample data, and for pixel data of areas $R_1$, $R_2$, and $R_3$ within an endoscopic image. In addition, FIG. 7A shows the endoscopic image so as to present a correspondence relation between the endoscopic image and the areas $R_1$, $R_2$, and $R_3$ in a visually recognizable manner. The areas $R_1$ and $R_2$ are lesion areas including lesion pixels. The area $R_3$ is a normal area including pixels imaging normal tissue. In FIGS. 7A and 7B, a vertical axis represents the hue value H (x, y), and a horizontal axis represents the saturation value S (x, y). FIG. 7A is a distribution diagram in which saturation values S (x, y) have not been corrected using the expression (3), and widely vary among individual pieces of the blood sample data. FIG. 7B is a distribution diagram in which saturation values S (x, y) have been corrected using the expression (3), so as to suppress the variation in the saturation values S (x, y) of the blood sample data.

As described above, normal mucous membranes in surfaces in an inflamed site drop off more with further symptom progression of IBD, such that the color of the inflamed site becomes a brighter red (a red with a higher saturation) so as to be closer to the blood color. Meanwhile, as the symptom of IBD is less serious, there is maintained a thicker layer of normal mucous membranes of surfaces in the inflamed site, such that the color of the inflamed site becomes a duskier red (a red with a lower saturation). Therefore, a more seriously inflamed site has a higher correlation with the blood color. In the example shown in FIGS. 7A and 7B, a symptom of IBD in the lesion area $R_1$ is more serious than a symptom of IBD in the lesion area $R_2$. As shown in FIG. 7A, in the uncorrected saturation values S (x, y), there are small differences between the lesion area $R_1$ and the lesion area $R_2$ because of the variation in the saturation value S (x, y) due to the unevenness of the illuminance of the illumination light. Nonetheless, it is possible to recognize that the saturation values of the lesion area $R_1$ are closer to the saturation values of the blood sample data than the saturation values of the lesion area $R_2$. Meanwhile, as shown in FIG. 7B, in the corrected saturation values S (x, y), there are more definite differences between the lesion area $R_1$ and the lesion area $R_2$, since the variation in the saturation value S (x, y) due to the unevenness of the illuminance of the illumination light is suppressed. Further, it is possible to more clearly recognize that the saturation values of the lesion area $R_1$ are closer to the saturation values of the blood sample data. Thus, the corrected saturation values S (x, y) reflect the severities of the inflamed sites more accurately than the uncorrected saturation values S (x, y). Hence, by correcting the saturation values S (x, y), it is possible to improve accuracy for evaluating the severity of the inflammation.

(S13c in FIG. 5)

Figure 8A:
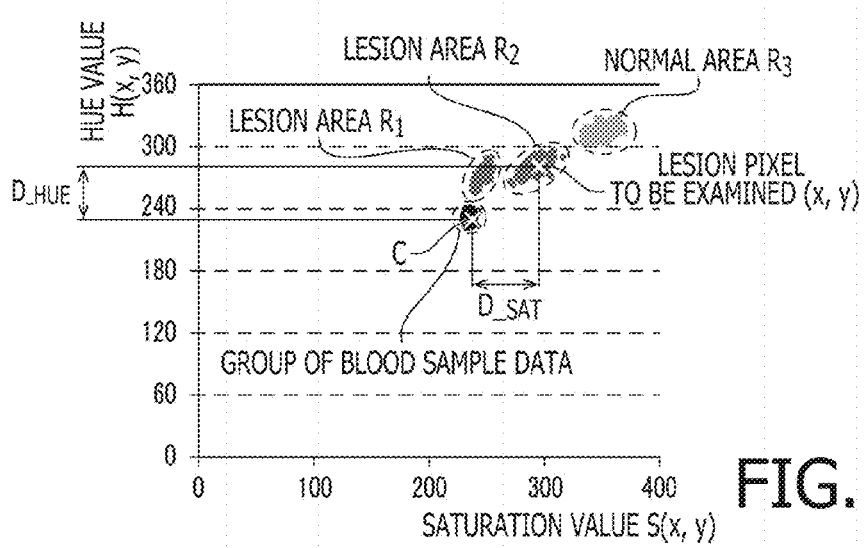
FIG. 8A is a diagram for illustrating how a hue distance and a saturation distance are defined for each lesion pixel in the embodiment according to aspects of the present invention.

In S13 (see FIG. 2), the processor 200 determines (calculates) a correlation value (a score) based on a general rule that data points, as located closer to each other on the distribution diagram shown in FIG. 7B, are more closely correlated with each other. FIG. 8A is a diagram for providing supplemental explanations regarding the process of determining the correlation value. In FIG. 8A in which the saturation values S (x, y) have been corrected, distances between the hue values H (x, y) of the lesion pixels and a hue value H ($x_C$, $y_C$) of a center of gravity C for a group of the blood sample data will be defined as hue distances $D\_{HUE}$. Further, distances between the corrected saturation values S (x, y) of the lesion pixels and a corrected saturation value S ($x_C$, $y_C$) of the center of gravity C for the group of the blood sample data will be defined as saturation distances $D\_{SAT}$.

Figure 8B:
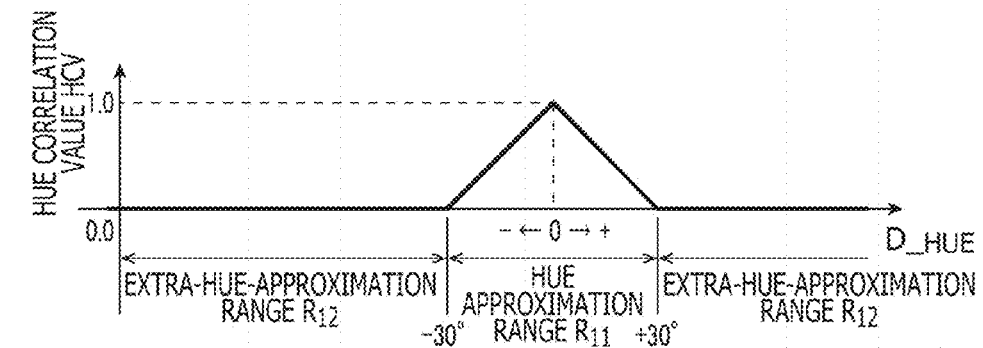
FIG. 8B is a hue correlation table for defining a relationship between the hue distances and hue correlation values in the embodiment according to aspects of the present invention.

FIG. 8B is a hue correlation table for defining a relationship between the hue distances $D\_{HUE}$ and hue correlation values HCV. For instance, the hue correlation values HCV may be normalized values (ranging from 0.0 to 1.0). The hue correlation table is stored in the memory 220a. In FIG. 8B, when the hue distance $D\_{HUE}$ for a lesion pixel is equal to 0, a hue value H (x, y) of the lesion pixel is coincident with the hue value H ($x_C$, $y_C$) of the center of gravity C for the group of the blood sample data. When the hue distance $D\_{HUE}$ for a lesion pixel is less than 0 (i.e., when having a negative value), a hue value H (x, y) of the lesion pixel is less than the hue value H ($x_C$, $y_C$) of the center of gravity C for the group of the blood sample data. When the hue distance $D\_{HUE}$ for a lesion pixel is more than 0 (i.e., when having a positive value), a hue value H (x, y) of the lesion pixel is more than the hue value H ($x_C$, $y_C$) of the center of gravity C for the group of the blood sample data. When the hue distance $D\_{HUE}$ for a lesion pixel is within a range from −30 degrees to +30 degrees (hereinafter referred to as "a hue approximation range $R_{11}$"), an inflamed site corresponding to the lesion pixel has a color equal to or close to the red of blood vessels. Therefore, as shown in FIG. 8B, in the hue approximation range $R_{11}$, the less an absolute value of the hue distance $D\_{HUE}$ is, the more the hue correlation value HCV is (i.e., the closer to 1 the hue correlation value HCV is). Meanwhile, when the hue distance $D\_{HUE}$ for a lesion pixel is in ranges out of the hue approximation range $R_{11}$ (hereinafter referred to as "extra-hue-approximation ranges $R_{12}$"), an inflamed site corresponding to the lesion pixel has a color that is no longer close to reds of blood vessels. Therefore, as shown in FIG. 8B, the hue correlation value HCV is equal to 0 evenly throughout the extra-hue-approximation ranges $R_{12}$.

In S13c, the processor 200 determines whether the hue distance $D\_{HUE}$ for the lesion pixel (x, y) to be examined is within the hue approximation range $R_{11}$.

(S13d in FIG. 5)

When determining that the hue distance $D\_{HUE}$ for the lesion pixel (x, y) to be examined is within the hue approximation range $R_{11}$ (S13c: Yes), the processor 200 provides the lesion pixel (x, y) to be examined with a hue correlation value HCV depending on the hue distance $D\_{HUE}$ in accordance with the hue correlation table (S13d).

(S13e in FIG. 5)

When determining that the hue distance $D\_{HUE}$ for the lesion pixel (x, y) to be examined is in the extra-hue-approximation ranges $R_{12}$ (S13c: No), the processor 200 provides the lesion pixel (x, y) to be examined with a hue correlation value HCV equal to 0 in accordance with the hue correlation table (S13e).

(S13f in FIG. 5)

Figure 8C:
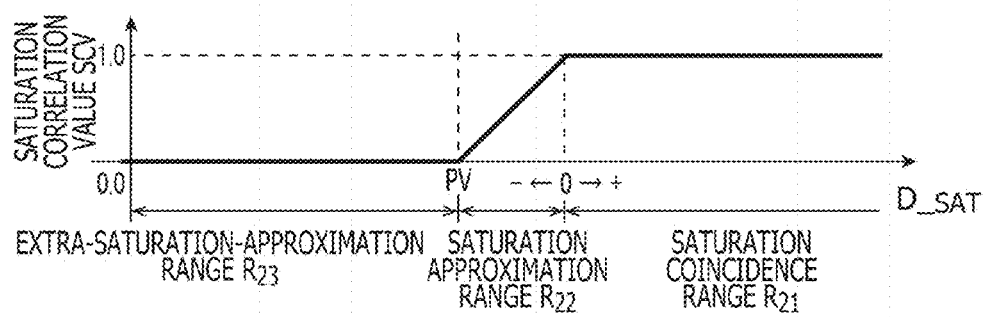
FIG. 8C is a saturation correlation table for defining a relationship between the saturation distances and saturation correlation values in the embodiment according to aspects of the present invention.

FIG. 8C is a saturation correlation table for defining a relationship between the saturation distances $D\_{SAT}$ and saturation correlation values SCV. For instance, the saturation correlation values SCV may be normalized values (ranging from 0.0 to 1.0). The saturation correlation table is stored in the memory 220a. In FIG. 8C, when the saturation distance $D\_{SAT}$ for a lesion pixel is equal to 0, a saturation value S (x, y) of the lesion pixel is coincident with the saturation value S ($x_C$, $y_C$) of the center of gravity C for the group of the blood sample data. When the saturation distance $D\_{SAT}$ for a lesion pixel is less than 0 (i.e., when having a negative value), a saturation value S (x, y) of the lesion pixel is less than the saturation value S ($x_C$, $y_C$) of the center of gravity C for the group of the blood sample data. When the saturation distance $D\_{SAT}$ for a lesion pixel is more than 0 (i.e., when having a positive value), a saturation value S (x, y) of the lesion pixel is more than the saturation value S ($x_C$, $y_C$) of the center of gravity C for the group of the blood sample data. When the saturation distance $D\_{SAT}$ for a lesion pixel is within a range equal to or more than 0 (hereinafter referred to as "a saturation coincidence range $R_{21}$"), an inflamed site corresponding to the lesion pixel is in a severely inflamed state where normal mucous membranes drop off, and the inflamed site has a color very close to a bright red of blood. Therefore, as shown in FIG. 8C, the saturation correlation value SCV is equal to 1 evenly throughout the saturation coincidence range $R_{21}$. Further, when the saturation distance $D\_{SAT}$ for a lesion pixel is within a range less than 0 and equal to or more than a predetermined value PV (hereinafter referred to as "a saturation approximation range $R_{22}$"), an inflamed site corresponding to the lesion pixel is in a severely inflamed state (nonetheless, its severity is less serious than the saturation coincidence range $R_{21}$) where normal mucous membranes drop off, and the inflamed site has a color close to the bright red of blood.

Therefore, as shown in FIG. 8C, in the saturation approximation range $R_{22}$, the less an absolute value of the saturation distance D_$_{SAT}$ is, the more the saturation correlation value SCV is (i.e., the closer to 1 the saturation correlation value SCV is). This is because the less the absolute value of the saturation distance D_$_{SAT}$ is, the closer to the bright red of blood the color of the inflamed site is. Moreover, when the saturation distance D_$_{SAT}$ for a lesion pixel is within a range less than the predetermined value PV (hereinafter referred to as "an extra-saturation-approximation range $R_{23}$"), an inflamed site corresponding to the lesion pixel has a thick layer of normal mucous membranes, and therefore has a dusky red. Hence, as shown in FIG. 8C, the saturation correlation value SCV is equal to 0 evenly throughout the extra-saturation-approximation range $R_{23}$.

In S13$f$, the processor 200 determines which range, the saturation distance D_$_{SAT}$ for the lesion pixel (x, y) to be examined is in, of the saturation coincidence range $R_{21}$, the saturation approximation range $R_{22}$, and the extra-saturation-approximation range $R_{23}$.

(S13$g$ in FIG. 5)

When determining that the saturation distance D_$_{SAT}$ for the lesion pixel (x, y) to be examined is in the saturation coincidence range $R_{21}$ (S13$f$: $R_{21}$), the processor 200 provides the lesion pixel (x, y) to be examined with a saturation correlation value SCV equal to 1 in accordance with the saturation correlation table (S13$g$).

(S13$h$ in FIG. 5)

When determining that the saturation distance D_$_{SAT}$ for the lesion pixel (x, y) to be examined is in the saturation approximation range $R_{22}$ (S13$f$: $R_{22}$), the processor 200 provides the lesion pixel (x, y) to be examined with a saturation correlation value SCV depending on the saturation distance D_$_{SAT}$ in accordance with the saturation correlation table (S13$h$).

(S13$i$ in FIG. 5)

When determining that the saturation distance D_$_{SAT}$ for the lesion pixel (x, y) to be examined is in the extra-saturation-approximation range $R_{23}$ (S13$f$: $R_{23}$), the processor 200 provides the lesion pixel (x, y) to be examined with a saturation correlation value SCV equal to 0 in accordance with the saturation correlation table (S13$i$).

(S13$j$ in FIG. 5)

In S13$j$, the processor 200 acquires a correlation value CV (ranging from 0.0 to 1.0) between the lesion pixel (x, y) to be examined and the blood sample data, by multiplying the hue correlation value HCV by the saturation correlation value SCV, both provided to the lesion pixel (x, y) to be examined. Thus, by calculating the correlation value between the lesion pixel (x, y) to be examined and the blood sample data based on two-dimensional information of the hue value and the saturation value, it is possible to acquire information that accurately represents the severity of the inflamed site.

[S14 in FIG. 2 (Integration of Correlation Values CV)]

In S14 (see FIG. 2), the processor 200 adds the correlation value CV determined in S13 for the lesion pixel (x, y) to be examined, to a summation of correlation values CV ever determined for individual lesion pixels. Thus, by integrating the correlation values CV for individual lesion pixels, it is possible to acquire an objective and reproducible evaluation value (i.e., evaluation information independent of a skill level of the operator) to quantify the severity of the inflammation.

[S15 in FIG. 2 (Color Replacement Process)]

Figure 9:
FIG. 9 is a conceptual diagram of a display color table in which correlation values are associated with predetermined display colors in the embodiment according to aspects of the present invention.

The memory 220$a$ stores a display color table in which the correlation values CV are associated with predetermined display colors. FIG. 9 is a conceptual diagram of the display color table. As shown in FIG. 9, the display color table has 11 levels, each associated with a predetermined display color, into which the correlation values CV (ranging from 0.0 to 1.0) are classified. In S15, the processor 200 replaces color information of the pixel (x, y) to be examined, with color information of a display color associated with the correlation value CV determined for the pixel (x, y) to be examined, in accordance with the display color table. For instance, as the correlation value CV determined for the pixel (x, y) to be examined is closer to 0, the color information of the pixel (x, y) to be examined may be replaced with color information of a colder color. Meanwhile, as the correlation value CV determined for the pixel (x, y) to be examined is closer to 1, the color information of the pixel (x, y) to be examined may be replaced with color information of a warmer color.

[S16 in FIG. 2 (Determination of Evaluation Completed for All Pixels)]

In S16, the processor 200 determines whether the evaluation of S11 to S15 has been completely performed for all the pixels. When determining that the evaluation has not been completely performed for all the pixels (i.e., there is left a pixel for which the evaluation has not been performed) (S16: No), the processor 200 goes back to S11.

[S17 in FIG. 2 (Display of Evaluated Image)]

When determining that the evaluation has been completely performed for all the pixels (S16: Yes), the processor 200 goes to S17, in which the processor 200 displays an evaluation image on the screen of the monitor 300. FIG. 10 exemplifies the evaluation image. As shown in FIG. 10, the evaluation image contains the endoscopic image in which the color information of each lesion pixel has been replaced in S15 (see FIG. 2). As shown in FIG. 10, the endoscopic image is a gray-scale image in which each pixel is provided with one of the 11-level colors depending on the severity of the inflamed site corresponding to each pixel. Therefore, the operator is allowed to visually recognize, without any difficulty, a location in the field of view and a severity of each individual inflamed site.

Further, in the evaluation image, a summation obtained by integrating the correlation values CV for all the lesion pixels is displayed as evaluation information (i.e., an evaluation value ranging from 0 to a value equivalent to the number of pixels) for the inflammation. In the example shown in FIG. 10, "SCORE: 1917" is displayed. Thus, according to the embodiment, the severity of the inflammation is evaluated and displayed as an objective and reproducible value. Therefore, the operator is allowed to objectively grasp the severity of the inflammation.

So far, the severity of the inflammation of IBD is divided into four levels according to medical evaluation e.g., using MAYO scores. In the meantime, recently, it has come to be known that there is a correlation between achievement of mucosal healing and remission duration. Therefore, it is considered effective for treatment for IBD to make a detailed evaluation of a mild case of IBD equivalent to MAYO 0 or MAYO 1. In the embodiment, the severity of the inflammation is shown as a numerical value ranging from 0 to a value equivalent to the number of pixels, so that the operator can conduct a more detailed evaluation of the severity of the inflammation. Accordingly, in the embodiment, it is possible to perform a more detailed evaluation even for a mild case of IBD equivalent to MAYO 0 or MAYO 1. Thus, the evaluation according to the embodiment is effective for treatment for IBD.

Hereinabove, the embodiment according to aspects of the present invention has been described. The present invention can be practiced by employing conventional materials, methodology and equipment. Accordingly, the details of such materials, equipment and methodology are not set forth herein in detail. In the previous descriptions, numerous specific details are set forth (such as specific materials, structures, chemicals, processes, etc.) in order to provide a thorough understanding of the present invention. However, it should be recognized that the present invention can be practiced without reapportioning to the details specifically set forth. In other instances, well known processing structures have not been described in detail, in order not to unnecessarily obscure the present invention.

Only an exemplary embodiment of the present invention and but a few examples of their versatility are shown and described in the present disclosure. It is to be understood that the present invention is capable of use in various other combinations and environments and is capable of changes or modifications within the scope of the inventive concept as expressed herein. For example, the following modifications are possible.

In the aforementioned embodiment, the correlation values CV are determined for the lesion pixels. However, the correlation values CV may be determined for all the pixels.

In the aforementioned embodiment, the CCD image sensor is employed as the solid-state image sensor 108. However, another solid-state image sensor such as a CMOS (Complementary Metal Oxide Semiconductor) image sensor may be employed.

In the aforementioned embodiment, employed is the solid-state image sensor 108 including the Bayer array color filter 108*b* of the primary colors R, G, and B. However, another solid-state image sensor may be employed that includes a color filter of complementary colors Cy (Cyan), Mg (Magenta), Ye (Yellow), and G (Green).

In the aforementioned embodiment, aspects of the present invention are applied to the IBD endoscopy. Nonetheless, aspects of the present invention may be applied to endoscopy for other diseases.

This application claims priority of Japanese Patent Application No. P2013-094730 filed on Apr. 26, 2013. The entire subject matter of the application is incorporated herein by reference.

What is claimed is:

1. A lesion evaluation information generator comprising:
an image data acquirer configured to acquire endoscopic color image data that represents an endoscopic image showing a lesion;
a memory; and
a processor configured to, when executing processor-executable instructions stored in the memory, provide:
a color information determiner configured to determine a hue value and a saturation value of each of pixels included in the endoscopic image based on the acquired endoscopic color image data;
a correlation value determiner configured to determine, for at least a part of the pixels of the endoscopic image, a correlation value that represents a correlation between color information of each individual pixel and reference color data, based on:
a hue correlation value that represents a correlation between the determined hue value of each individual pixel and a reference hue value of the reference color data; and
a saturation correlation value that represents a correlation between the determined saturation value of each individual pixel and a reference saturation value of the reference color data; and
an evaluation value generator configured to generate an evaluation value for evaluating a severity of the lesion in the endoscopic image, by deriving a summation of the correlation values from integrating the correlation value determined for each individual pixel.

2. The lesion evaluation information generator according to claim 1,
wherein the correlation value determiner is further configured to:
determine the hue correlation value based on a hue distance between the determined hue value of each individual pixel and the reference hue value of the reference color data on a two-dimensional coordinates defined with a coordinate axis for hue values and a coordinate axis for saturation values;
determine the saturation correlation value based on a saturation distance between the determined saturation value of each individual pixel and the reference saturation value of the reference color data on the two-dimensional coordinates defined with the coordinate axis for hue values and the coordinate axis for saturation values; and
determine the correlation value between color information of each individual pixel and the reference color data, based on the determined hue correlation value and the determined saturation correlation value.

3. The lesion evaluation information generator according to claim 2,
wherein the correlation value determiner is further configured to determine the correlation value between color information of each individual pixel and the reference color data, by multiplying the determined hue correlation value by the determined saturation correlation value.

4. The lesion evaluation information generator according to claim 3,
wherein the hue correlation value is a normalized value ranging from 0 to 1,
wherein when an absolute value of the hue distance is more than a predetermined distance value, the hue correlation value is equal to 0, and
wherein when the absolute value of the hue distance is equal to or less than the predetermined distance value, the less the absolute value of the hue distance is, the closer to 1 the hue correlation value is.

5. The lesion evaluation information generator according to claim 3,
wherein the saturation correlation value is a normalized value ranging from 0 to 1,
wherein when the determined saturation value is less than the reference saturation value of the reference color data, and the saturation distance is less than a predetermined saturation value, the saturation correlation value is equal to 0,
wherein when the determined saturation value is less than the reference saturation value of the reference color data, and an absolute value of the saturation distance is equal to or less than the predetermined saturation value, the less the absolute value of the saturation distance is, the closer to 1 the saturation correlation value is, and
wherein when the determined saturation value is equal to or more than the reference saturation value of the reference color data, the saturation correlation value is equal to 1 regardless of the absolute value of the saturation distance.

6. The lesion evaluation information generator according to claim 1,
wherein the color information determiner is further configured to determine the hue value and the saturation value of each individual pixel, by converting a color space of the acquired endoscopic color image data into one of an HSI color space and an HSV color space.

7. The lesion evaluation information generator according to claim 1,
wherein the color information determiner is further configured to determine an intensity value of each individual pixel included in the endoscopic image based on the acquired endoscopic color image data, as well as the hue value and the saturation value,
wherein the correlation value determiner comprises a saturation value corrector configured to correct the saturation value using the determined intensity value, and
wherein the correlation value determiner is further configured to determine the correlation value between the color information of each individual pixel and the reference color data, using the corrected saturation value.

8. The lesion evaluation information generator according to claim 7,
wherein the saturation value corrector is further configured to correct the saturation value based on a following expression:

$$\begin{bmatrix} INT_{-correction} \\ SAT_{-correction} \end{bmatrix} = \begin{bmatrix} \cos\theta & -\sin\theta \\ \sin\theta & \cos\theta \end{bmatrix} \begin{bmatrix} INT \\ SAT \end{bmatrix} + \begin{bmatrix} REFER_{-INT} \\ REFER_{-SAT} \end{bmatrix},$$

where
INT and SAT represent the intensity value and the saturation value, respectively,
REFER$_{INT}$ and REFER$_{SAT}$ represent a reference intensity value and the reference saturation value of the reference color data, respectively,
θ represents an angle corresponding to a correlation coefficient between the reference intensity value and the reference saturation value of the reference color data, and
INT$_{correction}$ and SAT$_{correction}$ represent a corrected intensity value and the corrected saturation value, respectively.

9. The lesion evaluation information generator according to claim 1,
wherein the reference color data is color data of blood.

10. The lesion evaluation information generator according to claim 1,
wherein the color information determiner comprises a lesion pixel determiner configured to determine whether each individual pixel is a lesion pixel imaging at least a part of the lesion, and
wherein the correlation value determiner is further configured to determine the correlation value only for each of pixels determined as lesion pixels.

11. The lesion evaluation information generator according to claim 1, further comprising a displayer configured to display the generated evaluation value.

12. The lesion evaluation information generator according to claim 11, further comprising a color information replacer configured to replace the color information of each individual pixel with replacement color information associated with the correlation value determined for each individual pixel,
wherein the displayer is further configured to display an image in which each individual pixel has the replacement color information associated with the correlation value.

13. A method configured to be implemented by a processor coupled with an image data acquirer configured to acquire endoscopic color image data that represents an endoscopic image showing a lesion, the method comprising:
determining a hue value and a saturation value of each of pixels included in the endoscopic image based on the acquired endoscopic color image data;
determining, for at least a part of the pixels of the endoscopic image, a correlation value that represents a correlation between color information of each individual pixel and reference color data, based on:
a hue correlation value that represents a correlation between the determined hue value of each individual pixel and a reference hue value of the reference color data; and
a saturation correlation value that represents a correlation between the determined saturation value of each individual pixel and a reference saturation value of the reference color data; and
generating an evaluation value for evaluating a severity of the lesion in the endoscopic image, by deriving a summation of the correlation values from integrating the correlation value determined for each individual pixel.

14. A non-transitory computer readable medium storing processor-executable instructions configured to, when executed by a processor coupled with an image data acquirer configured to acquire endoscopic color image data that represents an endoscopic image showing a lesion, cause the processor to:
determine a hue value and a saturation value of each of pixels included in the endoscopic image based on the acquired endoscopic color image data;
determine, for at least a part of the pixels of the endoscopic image, a correlation value that represents a correlation between color information of each individual pixel and reference color data, based on:
a hue correlation value that represents a correlation between the determined hue value of each individual pixel and a reference hue value of the reference color data; and
a saturation correlation value that represents a correlation between the determined saturation value of each individual pixel and a reference saturation value of the reference color data; and
generate an evaluation value for evaluating a severity of the lesion in the endoscopic image, by deriving a summation of the correlation values from integrating the correlation value determined for each individual pixel.

* * * * *